United States Patent
Kaneko et al.

(10) Patent No.: US 11,137,403 B2
(45) Date of Patent: Oct. 5, 2021

(54) METHOD FOR ESTIMATING GLEASON SCORE OF PROSTATE CANCER, METHOD FOR ESTIMATING PATHOLOGICAL STAGE, AND METHOD FOR ACQUIRING SUPPLEMENTARY INFORMATION, ALL ON THE BASIS OF SPECIFIC PSA CONTENT IN SPECIMEN

(71) Applicants: KONICA MINOLTA, INC., Chiyoda-ku (JP); HIROSAKI UNIVERSITY, Hirosaki (JP)

(72) Inventors: Tomonori Kaneko, Hachioji (JP); Takatoshi Kaya, Inagi (JP); Chikara Ohyama, Hirosaki (JP); Tohru Yoneyama, Hirosaki (JP); Yuki Tobisawa, Hirosaki (JP)

(73) Assignees: Konica Minolta, Inc., Tokyo (JP); HIROSAKI UNIVERSITY, Aomori (JP)

( * ) Notice: Subject to any disclaimer, the term of this patent is extended or adjusted under 35 U.S.C. 154(b) by 0 days.

(21) Appl. No.: 16/464,744

(22) PCT Filed: Nov. 29, 2017

(86) PCT No.: PCT/JP2017/042802
§ 371 (c)(1),
(2) Date: May 29, 2019

(87) PCT Pub. No.: WO2018/101327
PCT Pub. Date: Jun. 7, 2018

(65) Prior Publication Data
US 2019/0383818 A1    Dec. 19, 2019

(30) Foreign Application Priority Data

Nov. 29, 2016  (JP) .............................. JP2016-231322

(51) Int. Cl.
*G01N 33/574* (2006.01)
*G01N 21/64* (2006.01)

(52) U.S. Cl.
CPC ..... *G01N 33/57434* (2013.01); *G01N 21/648* (2013.01); *G01N 33/57488* (2013.01); *G01N 2021/6417* (2013.01); *G01N 2333/4724* (2013.01)

(58) Field of Classification Search
CPC .......... G01N 33/57434; G01N 21/648; G01N 33/57488; G01N 2021/6417; G01N 2333/4724; G01N 21/553; G01N 2333/96455; G01N 2400/40; G01N 2800/56; G01N 33/57484
See application file for complete search history.

(56) References Cited

U.S. PATENT DOCUMENTS

| | | | | |
|---|---|---|---|---|
| 9,285,368 B2* | 3/2016 | Yamashita | ....... | G01N 33/57434 |
| 10,196,694 B2* | 2/2019 | Yamashita | ....... | G01N 33/57434 |
| 2005/0221397 A1* | 10/2005 | Saito | ................ | G01N 33/57434 |
| | | | | 435/7.23 |
| 2011/0294141 A1* | 12/2011 | Yamashita | ....... | G01N 33/57434 |
| | | | | 435/7.4 |
| 2015/0140571 A1* | 5/2015 | Kaneko | ................ | G01N 33/566 |
| | | | | 435/7.1 |
| 2018/0348223 A1* | 12/2018 | Kaneko | ................ | G01N 33/543 |

FOREIGN PATENT DOCUMENTS

| | | |
|---|---|---|
| JP | 2011-137754 | 7/2011 |
| JP | 2013-509169 | 3/2013 |
| JP | 2013-076666 | 4/2013 |
| JP | 2015-518152 | 6/2015 |
| WO | WO 2010/064083 | 6/2010 |
| WO | WO 2010/090264 | 8/2010 |
| WO | WO 2013-161614 | 10/2013 |
| WO | WO 2017/056844 | 4/2017 |

OTHER PUBLICATIONS

Fukushima et al. (Glycobiology, "α1,2-Fucosylated and β-N-acetylgalactosaminylated prostate-specific antigen as an efficient marker of prostatic cancer" vol. 20, No. 4, pp. 452-460, published Dec. 11, 2009) (Year: 2009).*
Extended Search Report dated Aug. 21, 2019 issued in European Patent Application No. 17877115.0.
Kaya, et al., "High-sensitivity immunoassay with surface plasmon field-enhanced florescence spectroscopy using a plastic sensor chip: Application to quantitative analysis of total prostate-specific antigen and GalNAcbeta1-4GlcNAc-linked prostate-specific antigen for prostate cancer diagnosis", Analytical Chemistry, Feb. 3, 2015, pp. 1797-1803, vol. 87, No. 3.

(Continued)

*Primary Examiner* — Tracy Vivlemore
*Assistant Examiner* — Nam P Nguyen
(74) *Attorney, Agent, or Firm* — Cozen O'Connor

(57) ABSTRACT

The present invention provides methods that are for acquiring various types of supplementary information used for diagnosis or treatment of prostate cancer, and that can be implemented in a less-invasive manner at a low cost. Provided are, by measuring the content of prostate specific antigen (PSA) having a β-N-acetylgalactosamine residue at a non-reducing terminal of a sugar chain in a specimen, and comparing the measured value with a threshold value, (1) a method for estimating whether a Gleason score (primary pattern and secondary pattern) is not less than or less than a prescribed value, (2) a method for estimating whether the pathological stage (pT) is not less than or less than a prescribed value, and (3) a method for acquiring information for assessment indicating diagnosis or treatment should be actively conducted because a GS at gross total removal is expected to be higher than a GS at biopsy.

2 Claims, 4 Drawing Sheets

(56) References Cited

OTHER PUBLICATIONS

Hagiwara K., et al., "Wisteria floribunda agglutinin and its reactive-glycan-carrying prostate-specific antigen as a novel diagnostic and prognostic marker of prostate cancer", International Journal of Molecular Sciences, Jan. 26, 2017, pp. 1-16, vol. 18, No. 2, 261.
Yoneyama, T. et al., "Clinical significance of the LacDiNAc-glycosylated prostate-specific antigen assay for prostate cancer detection", Cancer Science, May 30, 2019, pp. 1-17, vol. 00.
T. Kaneko, "Development of a Prostate Cancer Diagnostic System Based on Surface Plasmon Field-Enhanced Fluorescence Spectroscopy", Konica Minolta Tech. Rep., Jan. 2016, vol. 13, pp. 73-78.
Y. Tobisawa, "Serum Lacdinac-PSA Determined by Surface Plasmon Field-Enhanced Fluorescence Spectroscopy (SPFS)—BAS", Journal of Urology, Apr. 2016, vol. 195, No. 4S, Suppl., pp. E15-E16.
International Search Report issued in the corresponding Appln. No. PCT/JP2017/042802.
Written Opinion issued in the corresponding Appln. No. PCT/JP2017/042802.

* cited by examiner

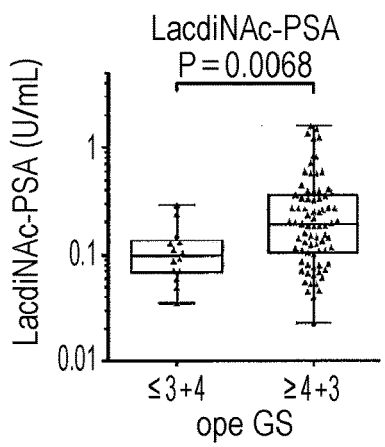
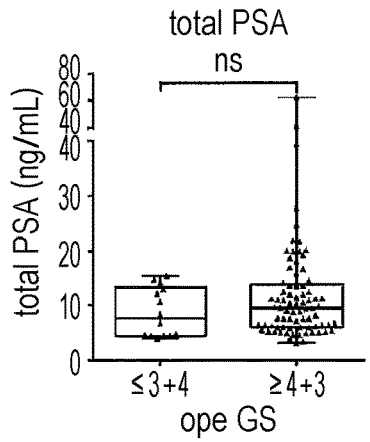
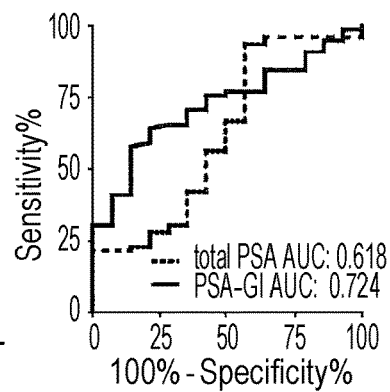
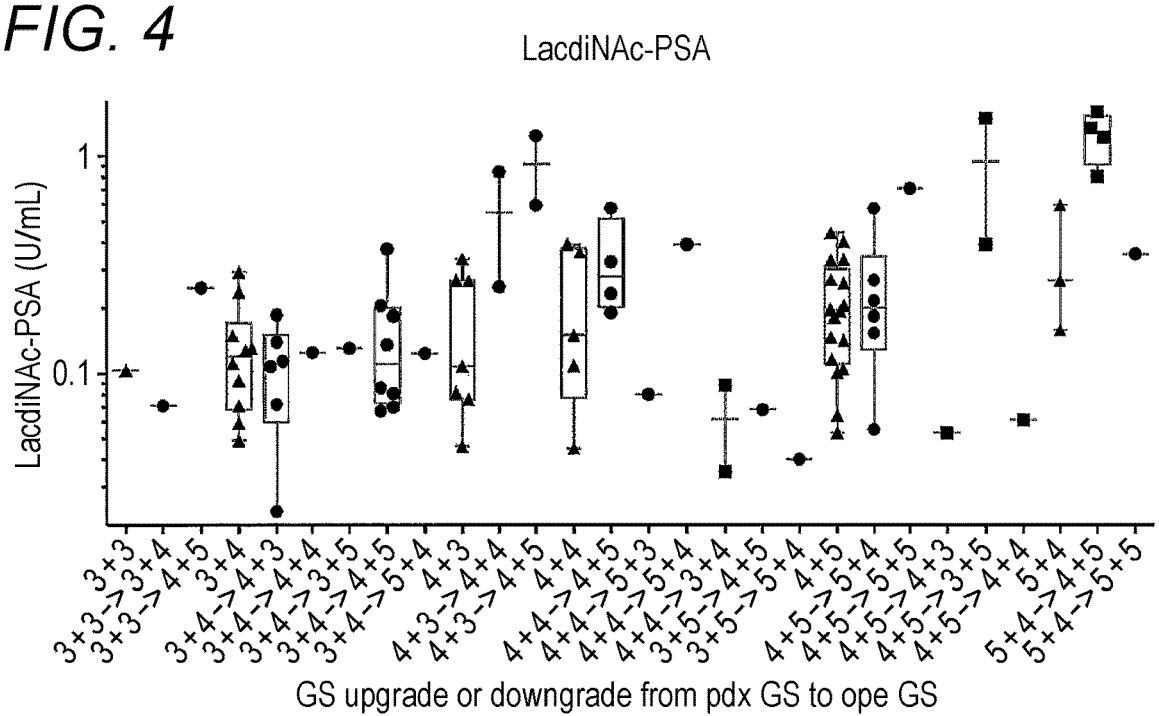
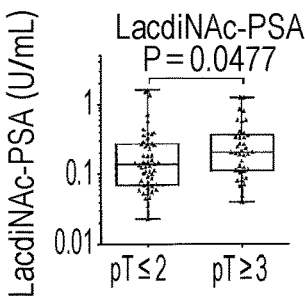
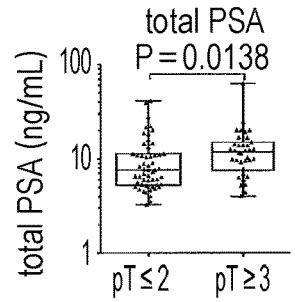
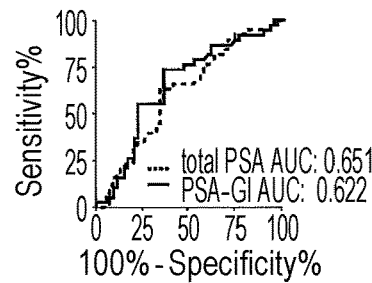

METHOD FOR ESTIMATING GLEASON SCORE OF PROSTATE CANCER, METHOD FOR ESTIMATING PATHOLOGICAL STAGE, AND METHOD FOR ACQUIRING SUPPLEMENTARY INFORMATION, ALL ON THE BASIS OF SPECIFIC PSA CONTENT IN SPECIMEN

RELATED APPLICATIONS

This is a U.S. National Phase Application under 35 USC 371 of International Application PCT/JP2017/042802 filed on Nov. 29, 2017.

This application claims the priority of Japanese application no. 2016-231322 filed Nov. 29, 2016, the entire content of which is hereby incorporated by reference.

TECHNICAL FIELD

The present invention relates to a Gleason score and a pathological stage (TNM staging), or other supplementary information used as an index for diagnosis or treatment of prostate cancer. More specifically, the present invention relates to methods of estimating a Gleason score and a pathological stage, or acquiring supplementary information for diagnosis or the like by using a specimen other than prostate cancer tissues.

BACKGROUND ART

Prostate cancer primarily occurs in men over 60 years of age, and in Western countries, it is the second leading cause of cancer-related death in men after lung cancer. For determination of a prostate cancer therapeutic strategy, the progress (pathological stage) and malignancy of the cancer serve as important indices. Of these indices, the malignancy of prostate cancer has a broad distribution that ranges from a state in which hardly any proliferation is recognized and follow-up without treatment is possible to a state in which the cancer has metastasized to bones or lymph nodes, and has caused exacerbation showing resistance to an antihormone agent. Therefore, it is desired to accurately assess the malignancy of prostate cancer.

As a staging that indicates the malignancy of prostate cancer, "Gleason score" (GS) which represents a diagnostic result of a cancer pathological tissue as a score has been widely used. Prostate cancer tissues can be classified into 5 stages of pattern 1 to pattern 5 based on the morphology and the mode of infiltrative growth (Gleason grading system). A Gleason score is a total value of a pattern given to an image of a tissue occupying the largest area based on the Gleason grading system (primary pattern) and a pattern given to an image of a tissue occupying the second largest area (secondary pattern, which may be the same as primary pattern depending on case), which images are obtained by observation of a certain pathological tissue under a microscope. Generally, it is considered that a GS of 2 to 6 indicates low malignancy, a GS of 7 indicates moderate malignancy, and a GS of 8 to 10 indicates high malignancy, and thus, whether or not the GS is 7 or higher serves as a principal criterion. Furthermore, since 2015, grade group (GG) is also used as an index of the malignancy instead of GS. GS of 6 or less corresponds to GG1, GS of 3+4 corresponds to GG2, GS of 4+3 corresponds to GG3, GS of 8 corresponds to GG4, and GS of 9 or 10 corresponds to GG5.

Meanwhile, to express progress (pathological stage) of prostate cancer, TNM staging (T: primary tumor, N: nearby lymph nodes, M: distant metastasis) is also widely used. As pathological staging, clinical staging (clinical staging before treatment: c) and pathological staging (histopathological staging after operation: p) are present. The former indicates a case in which the pathological staging is carried out based on information obtained before starting a treatment, and the latter indicates a case in which supplementary correction is made based on findings collected from an operation or a histopathological search. For example, with regard to the pathological staging (pT) of primary tumor, a case in which tumor is limited to an organ is designated as pT2, a case in which tumor has progressed into a region other than prostate is designated as pT3, and a case in which tumor has infiltrated bladder and rectum is designated as pT4 (there is no staging of pT1). Furthermore, regard to the pathological staging of nearby lymph nodes, a case in which a positive nearby lymph node is not recognized is designated as pN0, and a case in which metastasis in nearby lymph node (one or more) is recognized is designated as pN1. Furthermore, with regard to distant metastasis, a case in which distant metastasis is not recognized is staged M0 and a case in which distant metastasis is recognized is staged M1.

However, for histopathological diagnosis for deciding GS or the like described above, it is generally required that needle poking from rectum by using total 8 or more needles is carried out to collect prostate tissues (needle biopsy). For a patient, the needle biopsy is highly invasive, has a high risk of infection, and is very costly, and it also has a disadvantage that the diagnosis cannot be made if prostate cancer tissues are not touched by the needle.

Meanwhile, for prostate-related disorders such as prostate cancer and prostatic hyperplasia, studies are being made with a focus on their relationships with a prostate specific antigen (PSA) having a specific sugar chain that exists in a sample like blood of patients. Conventionally, methods of diagnosing whether or not a patient has prostate cancer by quantifying all PSAs (total PSA) contained in a sample and comparing the thus-obtained value with a threshold value, or by quantifying free type PSA (free PSA) not binding with α1-antichymotrypsin and comparing the ratio of the amount of the free type PSA with respect to the amount of all PSAs (free PSA/total PSA ratio) with a threshold value, have been known. However, in recent years, it has been gradually known that, depending on the disease affecting the patient, the properties of the sugar chains of PSAs vary, in other words, the amount (ratio) of a PSA having a specific sugar chain varies, and accordingly, several proposals have been made on methods that utilize this finding to diagnose whether or not a patient has prostate cancer or prostatic hyperplasia.

For example, Patent Literature 1 (WO 2010/064683) discloses a method in which the amount of a sugar chain having LacdiNAc (N-acetylgalactosamine-N-acetylglucosamine) and that of a sugar chain having LacNAc (galactose-N-acetylglucosamine) but not LacdiNAc are quantified for a PSA contained in a sample derived from a subject and, when the amount of the former is greater than 30% of the amount of the latter, the subject is determined to have prostate cancer.

Patent Literature 2 (JP 2011-137754 A) discloses a method in which the sugar chain structure of a PSA contained in a sample derived from a subject is analyzed and, when three or more sugar chains having LacdiNAc are present, the subject is determined to have prostate cancer.

Patent Literature 3 (WO 2010/090264) discloses a method in which a PSA having a β-N-acetylgalactosamine residue and/or a PSA having a fucose α (1,2) galactose residue in a sample (for example, serum) derived from a patient is/are quantified and, when the absolute amount thereof and/or the ratio thereof with respect to total PSA are/is larger than a prescribed cut-off value, the patient is determined to have prostate cancer, while the patient is determined to have prostatic hyperplasia when the absolute amount and/or the ratio is/are not larger than a prescribed cut-off value. It is described that the PSA having a β-N-acetylgalactosamine residue can be quantified using a lectin having an affinity for this residue, such as *Trichosanthes japonica* agglutinin-II (TJA-II) or *Wisteria floribunda* agglutinin (WFA) and that the PSA having a fucose α (1,2) galactose residue can be quantified using a lectin having an affinity for this residue, such as *Ulex europaeus* agglutinin-I (UEA-I) or TJA-II. It is also described that the above-described PSAs having the respective prescribed residues can each be quantified through adsorption and elution thereof, for example, by using a column in which a lectin is bound to a carrier (lectin affinity column).

Moreover, Patent Literature 4 (JP 2013-076666 A) discloses a method of quantifying a PSA having the same specific residue(s) as in Patent Literature 4 by a sandwich assay, such as Surface Plasmon-Field Enhanced Fluorescence Spectroscopy (SPFS), by using a solid-phase primary antibody for the PSA and a secondary capturing molecule obtained by labeling a lectin having a high affinity for the residue(s) of the PSA with a fluorescent pigment.

However, none of those Patent Literatures 1 to 4 describes a correlation between each method disclosed therein and the malignancy of prostate cancer, such as Gleason score. Particularly, in Example 1 of Patent Literature 3, while PSAs having the above-described specific sugar chains were quantified using TJA-II and it was shown that prostatic hyperplasia patients and prostate cancer patients can be distinguished from each other, it was analyzed that no significant difference was found in terms of the Gleason score. Further, in Example 2 of Patent Literature 3, PSAs having the above-described specific sugar chains were quantified by using WFA and it was analyzed that, for example, WFA showed the same tendency as TJA-II (the WFA binding rate was slightly lower but substantially correlates with that of TJA-II) and there is possibly a PSA having only a fucose α (1,2) galactose residue without a β-N-acetylgalactosamine residue. However, the quantification subject was only three specimens that are derived from prostate cancer patients, and no analysis was made with regard to the Gleason score. Furthermore, in Patent Literature 3, TJA-II and WFA are both exemplified as lectins having an affinity for β-N-acetylgalactosamine residue bound to a non-reducing terminal (terminal on the opposite side of a reducing terminal bound to a protein) of a sugar chain (see, paragraph [0020]). However, these lectins are different in terms of their affinity for other residues. That is, TJA-II is a lectin that shows a strong affinity for both β-N-acetylgalactosamine residues (GalNAcβ1→R; R represents other residue of a sugar chain or an amino acid residue of a protein) and fucose α(1,2) galactose residues (Fuc α1→2Gal β1→R) (see, paragraph [0022]). Meanwhile, WFA shows a strong affinity for β-N-acetylgalactosamine residues (GalNAcβ1→R), such as GalNAc(β1→4)Gal residue and GalNAc(β1→4)GlcNAc residue, but WFA does not have any affinity for fucose α (1,2) galactose residues (Fuc α1→2Gal β1→R) (see, paragraph [0023]).

CITATION LIST

Patent Literature

Patent Literature 1: WO 2010/064083
Patent Literature 2: JP 2011-137754 A
Patent Literature 3: WO 2010/090264
Patent Literature 4: JP 2013-076666 A

SUMMARY OF INVENTION

Technical Problem

As described above, conventional histopathological diagnosis that requires needle biopsy imposes a heavy burden on patients. Patients would be greatly benefited if a histopathological diagnosis result of prostate cancer, such as a Gleason score (GS) representing the malignancy of prostate cancer, could be obtained by a method that has low invasiveness and low cost as in the case of a blood test.

Furthermore, number of prostate cancer patients tends to increase all over the world in recent years, and an active treatment needs to be carried out first for prostate cancer patients with high malignancy. For example, even when GS is 7, grade group (GG) is 3 if GS is 4+3, or GG is 2 if GS is 3+4, showing a difference in malignancy evaluation, and it is determined that the former has higher malignancy and requires a more active treatment. Furthermore, the pathological staging (T) is highly useful for deciding therapeutic strategy if it can be known before operation, for example. If GS·GG can be estimated with high accuracy so as to allow malignancy discrimination without having needle biopsy, or pathological stage can be estimated before operation, they can bring enormous benefits for the treatment of prostate cancer.

Herein, part of the inventors of the present application found that, among PSAs contained in a specimen prepared from blood, with regard to content of a PSA that has an affinity for WFA, that is, PSA having a β-N-acetylgalactosamine residue at a non-reducing terminal of a sugar chain, there is a statistically significant difference between a sample group derived from prostate cancer patients having a "GS of 7 or higher" and other sample groups as well as between a sample group derived from prostate cancer patients having a "GS of 6 or lower" and other sample groups, and that, by setting an appropriate threshold value, whether the "GS is 7 or higher", or "GS 6 or lower" can be estimated with high accuracy. Part of the applicants of the present application filed a patent application of the invention for a method of estimating GS based on such finding (PCT/JP2016/075771, International publication date (=priority date): Sep. 28, 2015, hereinbelow, described as "prior application"). However, according to the method for estimating a GS of the prior application, it is not disclosed that a difference in GG or a difference in combination of primary pattern and secondary pattern (for example, GG3 when GS is 4+3 and GG2 when GS is 3+4) can be discriminated by the method of setting a threshold value. At the time of the prior application, a suitable method for estimating a difference in GG or the like is not known.

An object of the present invention is to provide a method that is for acquiring various types of supplementary information used for diagnosis or treatment of prostate cancer, and that can be implemented in a less invasive manner at a low cost.

Solution to Problem

The inventors of the present application found that, among PSAs contained in a specimen prepared from blood, content of a PSA that has an affinity for WFA, that is, PSA having a β-N-acetylgalactosamine residue at a non-reducing terminal of a sugar chain, and, more specifically, PSA having N-acetylgalactosamine-N-acetylglucosamine (β-GalNAc (1→4)GlcNAc) residue at a non-reducing terminal of a sugar chain (in the present specification, referred to as "LacdiNAc-PSA") is surprisingly related with a combination of primary pattern and secondary pattern of GS, for example, there is a statistically significant difference between a sample group derived from prostate cancer patients having a GS of 4+3 or higher and a sample group derived from prostate cancer patients having a GS of 3+4 or lower, and that, by setting an appropriate threshold value, whether the GS of a certain prostate cancer patient, from which a sample is collected, is 4+3 or higher, or 3+4 or lower can be estimated with high accuracy.

The inventors of the present invention also found that content of LacdiNAc-PSA in blood specimen has a statistically significant difference between prostate cancer patients having pathological stage (pT) or 3 or higher and prostate cancer patients having pT of 2 or lower, and that, by setting an appropriate threshold value, whether the pT of a certain prostate cancer patient, from which a specimen is collected, is 3 or higher, or 2 or lower can be estimated with high accuracy.

The inventors of the present invention also found that content of LacdiNAc-PSA in blood specimen has a statistically significant difference between a sample group for which an index related to pathological diagnosis like GS based on biopsy is underevaluated and other sample groups, or between a sample group for which the index is overevaluated and other groups. Underestimation of the index means that, when GS of tissues collected by biopsy is compared to GS of prostate cancer tissues obtained after gross total removal by operation (in other words, real one), the former has lower GS, and thus indicating a situation in which a more careful biopsy for diagnosis is preferably carried out or a more active treatment than a treatment considered from GS by biopsy is preferably carried out.

The present invention achieved by the above findings provides, according to the first aspect, a "method for estimating a Gleason score (GS) showing malignancy of prostate cancer as supplementary information for diagnosis or treatment of prostate cancer including measuring content of PSA having a β-N-acetylgalactosamine residue at a non-reducing terminal of a sugar chain in a specimen, and estimating that GS is 4+3 or higher when the measured value is not less than a threshold value, or estimating that GS is 3+4 or lower when the measured value is less than a threshold value." In the present specification, the method may be also referred to as a "method for estimating a Gleason score (GS)."

The present invention provides, according to the second aspect, a "method for estimating a pathological stage (pT) showing progress of prostate cancer as supplementary information for diagnosis or treatment of prostate cancer including measuring content of PSA having a β-N-acetylgalactosamine residue at a non-reducing terminal of a sugar chain in a specimen, and estimating that pT is 3 or higher when the measured value is not less than a threshold value, or estimating that pT is 2 or lower when the measured value is less than a threshold value." In the present specification, the method may be also referred to as a "method for estimating a pathological stage (pT)."

The present invention provides, according to the third aspect, a "method for acquiring, as supplementary information for diagnosis or treatment of prostate cancer, information for assessing degree of necessity of having diagnosis or treatment including measuring content of PSA having a β-N-acetylgalactosamine residue at a non-reducing terminal of a sugar chain in a specimen, and having information to assess such that a more accurate test than usual needs to be carried out for diagnosis of prostate cancer or an active therapeutic intervention needs to be carried out to treat prostate cancer when the measured value is not less than a threshold value." In the present specification, the method may be also referred to as a "method for acquiring information for assessment".

In other words, according to another aspect of the present invention, the present invention provides a "method for measuring content of PSA having a β-N-acetylgalactosamine residue at a non-reducing terminal of a sugar chain in a specimen including, at least, a step of binding a molecule having an affinity for β-N-acetylgalactosamine residue to the PSA." This measurement method can be used, in the same manner as described above, for estimating GS or pT, or acquiring information for assessment.

Furthermore, the threshold value used for each method of the present invention is different from threshold values used for a different purpose in prior art, such as the threshold value used for determining prostate cancer or prostatic hyperplasia as described in Patent Literature 3, or a threshold value used for estimating that Gleason score is 7 or higher or a threshold value for estimating that Gleason score is 6 or lower as described in aforementioned prior application. From this standpoint, the present invention can be distinguished from prior art or prior application.

Advantageous Effects of Invention

Each method of the present invention can be carried out not by tissue biopsy that imposes a heavy burden on patients by accompanying significantly harmful incidents like bleeding and infection but by a blood test that has low invasiveness, and thus follow-ups of cancer can be made and also QOL of a patient can be improved. Furthermore, due to lower cost than tissue biopsy, the blood test is effective for suppressing medical cost.

Furthermore, when desirably combined with the pathological stage that is estimated by the method of the present invention or supplementary information that is acquired by the method of the method of the present invention, the Gleason score that is estimated by the method of the present invention allows more accurate assessment of true malignancy of prostate cancer before operation, and it is considered that the Gleason score can be used for various cases like modification of therapeutic strategy, assessing an application of active surveillance, or the like.

BRIEF DESCRIPTION OF DRAWINGS

FIG. 1 is a schematic diagram illustrating reactions taking place in a measurement region 38 inside a flow channel 36 during quantification of a LacdiNAc-PSA 100 contained in a specimen using an SPFS measuring member 16.

FIG. 2 is a schematic diagram illustrating general embodiments of an SPFS system 1.

Figure 1A:
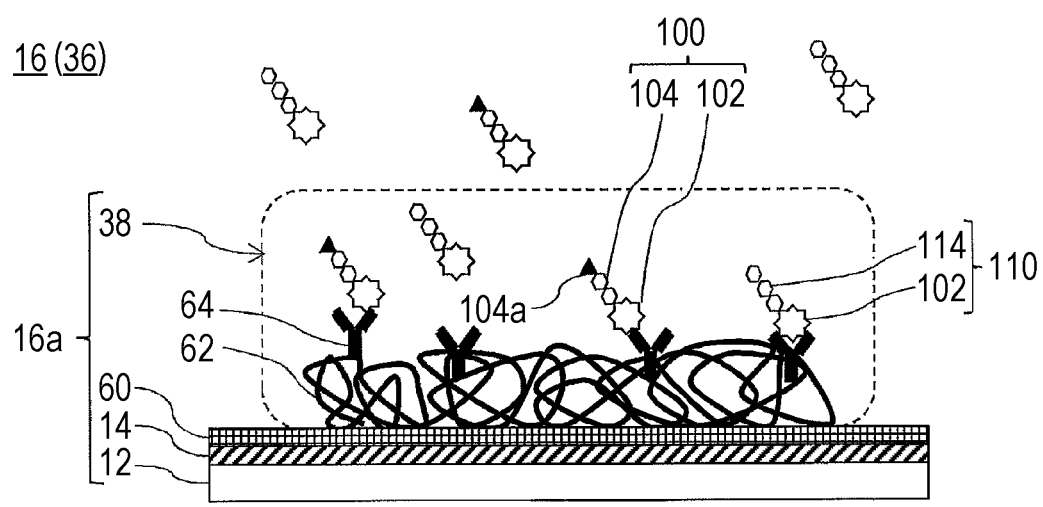
FIG. 1A: The reaction in the capturing step performed for binding the LacdiNAc-PSA 100 to an anti-PSA antibody 64 carried on a support 62.

An embodiment in which the metal thin film 14 is formed on an upper surface of a transparent planar substrate 13 that can be separated from the dielectric member 12 and the plasmon excitation sensor 16a is constituted by the transparent planar substrate 13, the metal thin film 14 and the measurement region 38.

FIG. 3 is, for a patient group having GS of 3+4 or lower and a patient group having GS of 4+3 or higher with regard to removed prostate tissues in Examples, FIG. 3A: a box plot when distribution of LacdiNAc-PSA concentration in a blood specimen is compared, FIG. 3B: a box plot when distribution of total PSA concentration in a blood serum specimen is compared, and FIG. 3C: an ROC curve established from those results. Ope GS: Gleason score after an operation for removing prostate. PSA-Gi: LacdiNAc-PSA.

FIG. 4 is a box plot obtained by, in Examples, classifying patients depending on transition from the GS at biopsy (combination of primary pattern and secondary pattern) to GS after gross total removal by operation and comparing LacdiNAc-PSA concentration in blood serum specimen of each patient group.

FIG. 5 is, in Examples, for a patient group having pT of 2 or lower and a patient group having pT of 3 or higher, FIG. 5A: a box plot when distribution of LacdiNAc-PSA concentration in a blood specimen is compared, FIG. 5B: a box plot when distribution of total PSA concentration in a blood serum specimen is compared, and FIG. 5C: an ROC curve established from those results. PSA-Gi: LacdiNAc-PSA.

Figure 6:
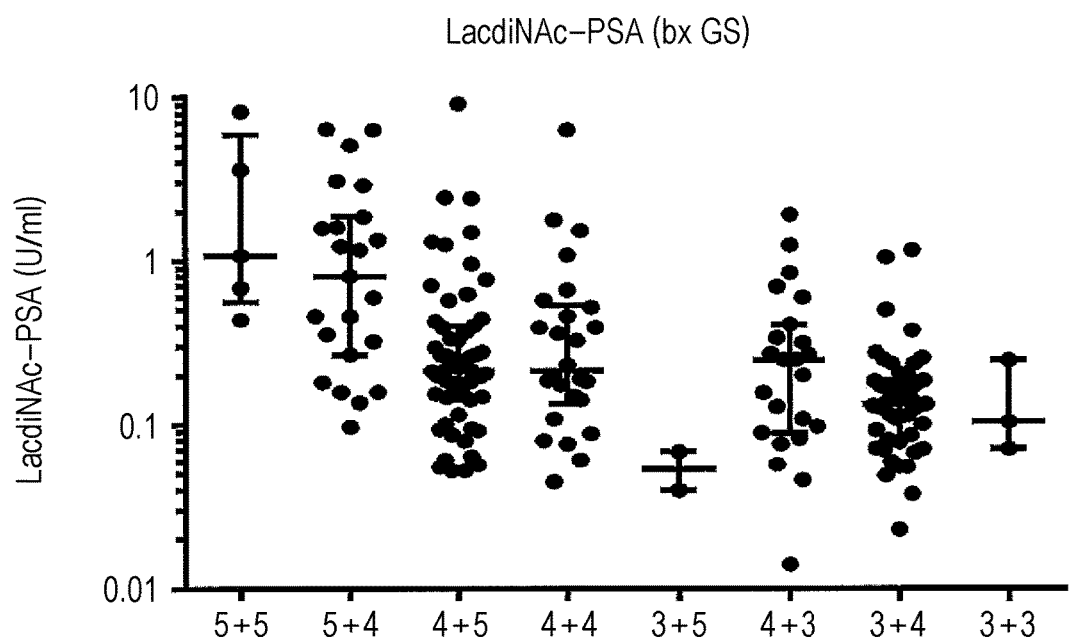

FIG. 6 is a box plot obtained by, in Reference Example, classifying the patients depending on GS at biopsy (combination of primary pattern and secondary pattern) and comparing LacdiNAc-PSA concentration in blood serum specimen of each patient group.

Figure 7:
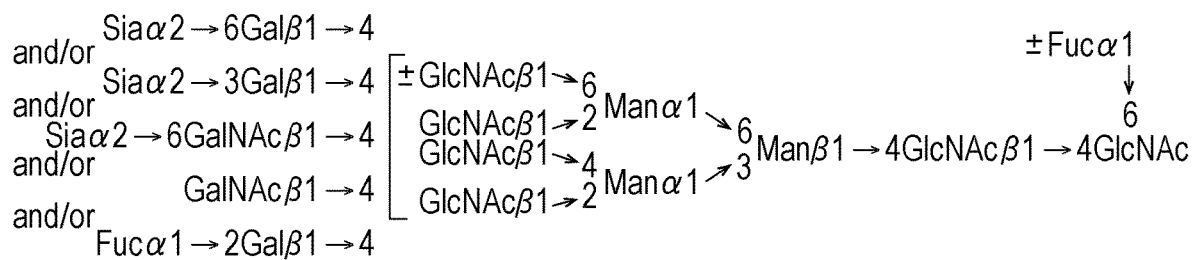

FIG. 7 is an estimated structural formula of a sugar chain possessed by PSA that is contained in a blood serum specimen of a prostate cancer patient. Source: Fukushima et al. Glycobiology, 20, 4, 452-460 (2010).

DESCRIPTION OF EMBODIMENTS

As a subject for quantification in the present invention, the PSA having a β-N-acetylgalactosamine residue (β-GalNAc residue) at a non-reducing terminal of a sugar chain is, specifically, PSA having a β-N-acetylgalactosamine-(1→4)-N-acetylglucosamine residue (GalNAc(β1→4)GlcNAc residue) at a non-reducing terminal of a sugar chain. This PSA as a subject for quantification in the present invention is described as "LacdiNAc-PSA". In FIG. 7, the estimated structural formula of a sugar chain possessed by PSA that is contained in a blood serum specimen of a prostate cancer patient is shown. It is believed that the PSA as a subject for quantification in the present invention has, other than a sugar chain in which a GalNAc residue binds to, via β1→4 bond, to a GlcNAc residue, a sugar chain with sialylated terminal or a sugar chain having a fucose at the terminal.

The method for estimating a Gleason score (GS) according to the present invention is a method including measuring content of PSA having a β-N-acetylgalactosamine residue at a non-reducing terminal of a sugar chain (LacdiNAc-PSA) in a specimen, and estimating that GS is 4+3 or higher when the measured value is not less than a threshold value, or estimating that GS is 3+4 or lower when the measured value is less than a threshold value. It can be said that the GS estimated by this method is a GS of tissues of prostate that are obtained after gross total removal by operation, and it reflects real (true) malignancy of prostate cancer compared to a GS of tissues collected by biopsy before operation. "GS is 4+3 or higher" indicates, specifically, that combination of primary pattern and secondary pattern of GS is 4+3, 5+3, 4+4, 3+5, 5+4, 4+5, or 5+5, in other words, the grade group (GG) is 3 (GS is 4+3), 4 (GS is 8) or 5 (GS is 8 or 10). "GS is 3+4 or lower" indicates, specifically, that combination of primary pattern and secondary pattern of GS is 3+4, 4+2, 3+3, or 2+4, or, in rare cases, 3+2 or 2+3, in other words, GG is 2 (GS is 3+4) or 1 (GS is 6 or lower).

The method for estimating a GS of the present invention can be modified so as to not only estimate whether or not GS of prostate tissues obtained after gross total removal by operation is 4+3 or higher, or 3+4 or lower, but also to estimate, for a GS of tissues of prostate obtained after gross total removal by operation or a GS of tissues collected by biopsy before operation, whether the GS is not less than or not more than other combination of primary pattern and secondary pattern. Combination of primary pattern and secondary pattern of GS is, in the order of high malignancy to low malignancy, 5+5, 5+4, 4+5, 5+3, 4+4, 3+5, 4+3, 3+4, 4+2, 3+3, 2+4, 3+2, and 2+3. For example, when GS is "4+5 or higher", it means a combination of 4+5 and higher malignancy, that is, 4+5, 5+4 and 5+5.

Furthermore, the method for estimating a GS of the present invention can be converted or broadened to a method for estimating a GG. Namely, the method for estimating a GG is a method including measuring content of LacdiNAc-PSA in a specimen, and estimating that GG is 3 or higher when the measured value is not less than a threshold value, or estimating that GG is 2 or lower when the measured value is less than a threshold value. Furthermore, by setting an appropriate threshold value, the method for estimating a GG of the present invention allows an embodiment in which estimation is made such that GG is 4 or higher or GG is 5 or higher.

The method for estimating a pathological stage (pT) according to the present invention is a method including measuring content of PSA having a β-N-acetylgalactosamine residue at a non-reducing terminal of a sugar chain (LacdiNAc-PSA) in a specimen, and estimating that pT is 3 or higher when the measured value is not less than a threshold value, or estimating that pT is 2 or lower when the measured value is less than a threshold value. In combination with GS, pT is used as an index for evaluating a risk related to recurrence of prostate cancer, and a "Nomogram" in which their correlation is expressed in terms of probability (Partin nomogram as a representative example) or "Risk classification" based on it is used for selecting a therapeutic method or the like.

The method for acquiring information for assessment for diagnosis or treatment according to the present invention is a method including measuring content of PSA having a β-N-acetylgalactosamine residue at a non-reducing terminal of a sugar chain (LacdiNAc-PSA) in a specimen, and having information to assess such that a more accurate test than usual needs to be carried out for diagnosis of prostate cancer or an active therapeutic intervention needs to be carried out to treat prostate cancer when the measured value is not less than a threshold value. The expression "more accurate test than usual" means that, by increasing the number of needles used for biopsy or increasing the number of biopsy (rebiopsy), possibility of collecting prostate cancer tissues is increased, or, by combining a test other than needle biopsy, it is made difficult to have not-finding or underestimation of prostate cancer, for example. Furthermore, the expression "active therapeutic intervention" means that, for a patient already having a treatment based on chemotherapy (administration of anti-cancer agent and/or hormone), radiation therapy is further applied or gross total removal of prostate tissues is carried out by an operation, or, for a patient under surveillance therapy, chemotherapy, radiation therapy, or operation is carried out, for example.

In the present invention, the supplementary information for diagnosis or treatment of prostate cancer is helpful for diagnosis of prostate cancer. Accordingly, the method of the present invention can be expressed as a method by which a machine or a person other than doctor classifies data that are helpful for diagnosis to be made by a doctor.

With regard to the three methods of the present invention that are described above, any one method can be carried out, or two methods or three methods can be carried out simultaneously for one specimen. When plural methods are carried out simultaneously, complex information for diagnosis or treatment of prostate cancer can be acquired, and thus desirable.

The "specimen" is a material that is collected from a subject to which each method of the present invention is applied and used for measuring content of LacdiNAc-PSA, and examples of the specimen include a liquid specimen like blood, urine, and ascites which can be collected by a non-invasive or low-invasive technique. For example, a specimen prepared from anti-coagulated whole blood, preferably blood serum or blood plasma, is suitable as a specimen in the present invention. If necessary, depending on a method of quantifying LacdiNAc-PSA, the specimen can be also a sample that is prepared by adding a liquid for dilution, a reagent, or the like.

The subject for applying each method of the present invention, that is, a subject from which a specimen is collected, is typically a human. However, it may be also a mammal other than human like a model animal having human disorder. As a human subject, it is typically a patient having confirmative diagnosis of prostate cancer, or a person having a possibility of development into prostate cancer and a person required to know the malignancy of prostate cancer. Examples of a mammal subject other than human include a model animal like mouse and rat that are induced to have an onset of prostate cancer.

[Method for Quantification]

The method for measuring content of LacdiNAc-PSA in a specimen is not particularly limited as long as a measured value having accuracy allowing comparison with a prescribed threshold value is obtained, and various quantification methods can be used.

As a method for quantifying LacdiNAc-PSA, a method which can be carried out by a relatively convenient means and includes a step of binding a molecule having an affinity for a β-N-acetylgalactosamine residue (β-GalNAc residue-affinity molecule) to LacdiNAc-PSA is preferable, but, methods other than that, for example, a method based on mass analysis can be also used.

β-GalNAc Residue-Affinity Molecule

As the β-GalNAc residue-affinity molecule, a lectin having an affinity for β-GalNAc residue (β-GalNAc residue-affinity lectin) or an antibody whose epitope is β-GalNAc residue (anti β-GalNAc residue) can be used.

β-GalNAc Residue-Affinity Lectin

A lectin is a protein having an affinity for a specific sugar residue, that is, a protein that recognizes and binds to a specific sugar residue, and a large variety of lectins (also may be referred to as "agglutinins") derived from various organisms are known. The sugar residue for which a lectin has an affinity varies depending on the type of the lectin, and most lectins have an affinity not just for one sugar residue but for plural sugar residues (however, the affinity for a specific sugar residue is strong and the affinity for other sugar residues is weak). Generally speaking, while antibodies whose epitope is a specific sugar residue in a sugar chain, such as an anti β-GalNAc antibody, are difficult to prepare, β-GalNAc residue-affinity lectins not only are inexpensive and available in a large amount but also have excellent stability and can be stored over a long time, and therefore, β-GalNAc residue-affinity lectins are preferred as β-GalNAc residue-affinity molecules.

Various β-GalNAc residue-affinity lectins have been known, and it is also possible that a GalNAc residue-affinity lectin will be isolated from a new organism. In the present invention, any lectin can be used as long as it has a sufficiently strong affinity for β-GalNAc residue, that is, the lectin has no affinity for other sugar residues, or the lectin has an affinity for other sugar residues as well but the affinity for other sugar residues is sufficiently weaker than the affinity for GalNAc residue (for example, the binding constant is lower by several orders), and a LacdiNAc-PSA can be quantified with sufficient accuracy.

Specific examples of β-GalNAc residue-affinity lectins include *Wisteria floribunda* agglutinin (WFA), soybean agglutinin (SBA), *Vicia Villosa* lectin (VVL), and *Trichosanthes japonica* agglutinin-II (TJA-II). These lectins can be separated (extracted) and purified from the organisms, for example, seeds from which each lectin is derived, or they can be obtained as a commercially available product.

WFA is sometimes denoted as "*Wisteria floribunda* lectin" (WFL) and it is a lectin (agglutinin) derived from *Wisteria floribunda*. WFA has an affinity for N-acetyl-D-galactosamine residues (GalNAc), that is, for both α-N-acetyl-D-galactosamine residue (α-GalNAc) and β-N-acetyl-D-galactosamine residue (β-GalNAc), and is capable of binding to, for example, GalNAc(α1→6)Gal residue, GalNAc(α1→3)Gal/GalNAc residue, GalNAc(β1→4)Gal residue, and GalNAc(β1→4)GlcNAc residue, which are present at a non-reducing terminal of a sugar chain, as well as GalNAc-Ser/Thr (serine or threonine) and the like that are present at a reducing terminal of a sugar chain. In addition, WFA has a relatively weak affinity for lactose and galactose. Furthermore, β-GalNAc residue to which WFA and other β-GalNAc residue-affinity lectins that are described below are bound are not modified by sialylation or the like.

SBA is a lectin (agglutinin) derived from soybean. SBA also has an affinity for both α-N-acetyl-D-galactosamine residue (α-GalNAc) and β-N-acetyl-D-galactosamine residue (β-GalNAc) (affinity for the former is slightly stronger than the affinity for the latter). SBA is capable of binding to, for example, GalNAc(α1→3)Gal residue, GalNAc(β1→4) Gal residue, and GalNAc(β1→4)GlcNAc residue, which are present at a non-reducing terminal of a sugar chain. Furthermore, SBA has a relatively weak affinity for galactose as well.

VVL is sometimes denoted as "*Vicia villosa* agglutinin" (VVA) and is a lectin (agglutinin) derived from hairy vetch. VVL also has an affinity for both α-N-acetyl-D-galactosamine residue (α-GalNAc) and β-N-acetyl-D-galactosamine residue (β-GalNAc), and is capable of binding to, for example, GalNAc(α1→3)Gal residue, GalNAc(β1→4) Gal residue, and GalNAc(β1→4)GlcNAc residue, which are present at a non-reducing terminal of a sugar chain.

TJA-II is one of the lectins (agglutinin) that are derived from *Trichosanthes japonica*. TJA-II also has an affinity for N-acetyl-D-galactosamine residues (GalNAc) like 3-N-acetyl-D-galactosamine residue (β-GalNAc) and is capable of binding to GalNAc(β1→4)GlcNAc residue which is present at a non-reducing terminal of a sugar chain. Furthermore, TJA-II has a relatively strong affinity for fucose (α1→2) galactose residue as well.

Embodiments of Method for Quantification of LacdiNAc-PSA

A representative embodiment (first quantification method) of the method for quantification of LacdiNAc-PSA including a step of binding a β-GalNAc residue-affinity molecule to LacdiNAc-PSA is, for example, a method which includes allowing a β-GalNAc residue-affinity molecule along with a molecule specifically binding to other PSA to bind to a LacdiNAc-PSA and thereby forming a sandwich type complex composed of these three molecules. Specific examples of this sandwich type complex include sandwich type complexes composed of an anti-PSA antibody whose epitope is a PSA protein carried (immobilized) on a support, a LacdiNAc-PSA, and a fluorescence-labeled β-GalNAc affinity lectin or anti GalNAc antibody.

The "anti-PSA antibody" can be prepared by a commonly used method, or it can be purchased as a commercially available product. From the standpoint of the measurement stability, a monoclonal antibody is used more preferably than a polyclonal antibody. Furthermore, in order not to prevent a fluorescence-labeled lectin from recognizing and binding to a specific sugar residue (β-GalNAc in the present invention) in a sugar chain, it is preferred to use an antibody whose epitope is a protein moiety, not a sugar chain, of PSA. As such anti-PSA monoclonal antibodies whose epitope is a PSA protein, for example, clones such as PS2, PS3, PS4, PS5, PS6, PS15, 2H9, 3B4, 5A6, 5G6, 8G4, 9A8, 9G2, PS1, 8A6, 2H9, 1H12, and No. 79 are known and they are also commercially available. The anti β-GalNAc antibody can also be prepared in the same manner and, for example, clones such as 100-2H5-A, 114-2H12-C, 259-2A1, 273-3F2, 99-2A5-B, and SMLDN1.1 are known.

The fluorescence-labeled β-GalNAc-affinity lectin can be prepared by binding a desired fluorescent material to the above-described β-GalNAc-affinity lectin in accordance with a commonly used method and, in this process, a commercially available fluorescent material labeling kit or the like can be used as well. The fluorescent material is not particularly limited and, for example, a fluorescent pigment capable of emitting an appropriate fluorescence in SPFS can be used. The fluorescence-labeled anti β-GalNAc antibody can also be prepared in the same manner.

As a method of quantifying the amount of the sandwich type complex containing the β-GalNAc residue-affinity molecule as described above, that is, the LacdiNAc-PSA content in a specimen, Surface Plasmon-Field Enhanced Fluorescence Spectroscopy (SPFS), which is known as a method capable of quantifying a measurement subject with high sensitivity and high accuracy, is appropriate. The LacdiNAc-PSA contained in a specimen can be quantified based on the intensity of fluorescence emitted from the fluorescent material contained in the sandwich type complex, which is measured by SPFS.

Another embodiment (second quantification method) of the LacdiNAc-PSA quantification method including the step of binding a β-GalNAc residue-affinity molecule to a LacdiNAc-PSA includes a method which utilizes a column loaded with a carrier bound with a lectin having an affinity for the β-GalNAc residue (lectin affinity column). That is, a specimen is applied to the lectin affinity column to bind the LacdiNAc-PSA to the lectin and, subsequently, a hapten sugar-containing elution buffer is applied thereto to dissociate the LacdiNAc-PSA and a fraction containing the LacdiNAc-PSA is recovered, after which the LacdiNAc-PSA content in the fraction can be measured by immunoassay. In the second quantification method, for the quantification of LacdiNAc-PSA in the LacdiNAc-PSA-containing fraction, since substantially all of the PSAs contained in the fraction have the β-GalNAc residue, it is not required to use a labeled β-GalNAc residue-affinity molecule (lectin), and a labeled anti-PSA antibody whose epitope is a PSA protein can be used. The LacdiNAc-PSA in the LacdiNAc-PSA-containing fraction can be quantified by, for example, a chemiluminescent enzyme immunoassay in which an immunocomplex composed of an anti-PSA antibody-bound magnetic particle/a PSA/an alkaline phosphatase-labeled anti-PSA antibody is formed and the emission intensity is subsequently measured with an addition of a chemiluminescent substrate, or by SPFS method in which an immunocomplex composed of an immobilized anti-PSA antibody/a PSA/a fluorescence-labeled anti-PSA antibody is formed and the fluorescence intensity is subsequently measured by SPFS.

SPFS Measurement Method

SPFS is a method which utilizes a phenomenon that, when a metal thin film formed on the upper surface of a dielectric member is irradiated, from the back side (the side in contact with the dielectric member), with an incident light at an angle that causes attenuated total reflection (ATR), an evanescent wave generated on the surface (the side on which a measurement region is formed) by the incident light transmitting through the metal thin film is enhanced by several ten times to several hundred times due to resonance with surface plasmon, and uses the thus-enhanced evanescent wave as an excitation light so as to allow a fluorescent material labeling a subject to be measured that is captured in the measurement region to emit efficiently the fluorescence. The subject to be measured in a specimen can be quantified by measuring the intensity of the fluorescence, and the measured value of each specimen is compared with a measured value of fluorescence intensity value measured for a standard specimen having known concentration, and thus the measured value can be converted into the content (concentration) of the subject to be measured in the specimen. SPFS performed in this manner is extremely sensitive as compared to conventional fluorescent labeling methods such as ELISA, and therefore it is suitable as a quantification method used in those cases in which the concentration of the subject to be measured is extremely low in a specimen.

Furthermore, in the present invention, each method is carried out based on the content (concentration) of a LacdiNAc-PSA in a specimen. However, it is also possible to, for an analysis, directly use a "measured value" obtained by a quantification method such as SPFS in accordance with a prescribed measurement protocol without converting the "measured value" into "concentration" expressed in a prescribed unit such as ng/mL or U (unit)/mL. For example, in SPFS, measured values of fluorescence intensity are usually expressed in an arbitrary unit (a.u.). However, a threshold value in this arbitrary unit may be set based on the measured values expressed in the arbitrary unit that are obtained for each specimen under the same condition, and the Gleason score may be estimated from the measured value of each specimen measured under the same condition.

A general embodiment in which a sandwich type complex composed of an anti-PSA antibody/a LacdiNAc-PSA/a fluorescence-labeled β-GalNAc residue-affinity molecule is formed and the intensity of fluorescence emitted from this complex (fluorescent material) is subsequently measured by SPFS will now be described on the basis of FIG. 1.

Figure 1B:
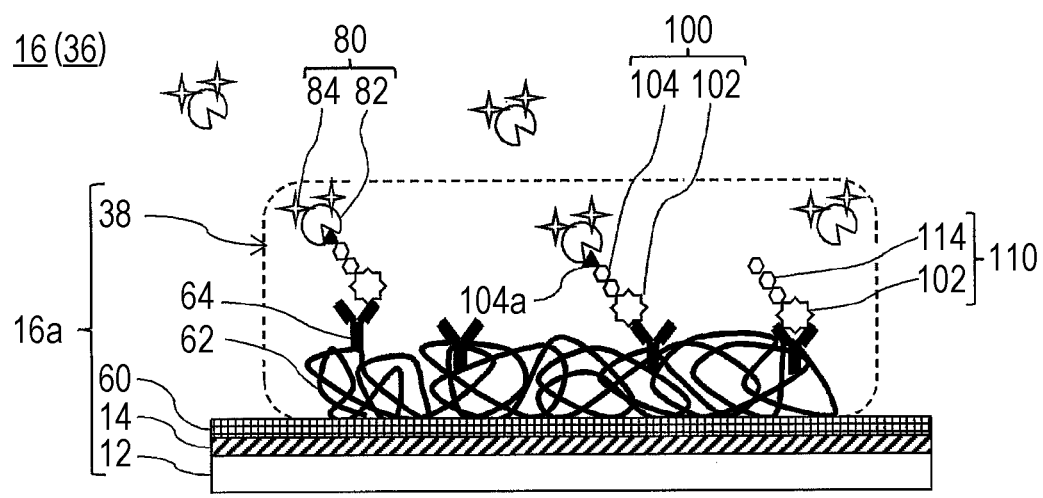
FIG. 1B: The reaction in the labeling step performed for binding a fluorescence-labeled β-GalNAc affinity molecule 80 to the LacdiNAc-PSA 100 captured on the anti-PSA antibody 64.

The steps performed in implementing SPFS can be divided into the steps of "pre-measurement stage" and the steps of "measurement stage". The steps of the pre-measurement stage are the steps performed up to the formation of a sandwich type complex composed of an anti-PSA antibody/an LacdiNAc-PSA/a fluorescence-labeled β-GalNAc residue-affinity molecule, and they typically include the step of allowing a LacdiNAc-PSA 100 to bind to an anti-PSA antibody 64 and thereby capturing the LacdiNAc-PSA 100 in the measurement region 38 (capturing step) as illustrated in FIG. 1A, and the step of fluorescently labeling the LacdiNAc-PSA 100 by allowing a fluorescence-labeled β-GalNAc residue-affinity molecule 80 to bind thereto as illustrated in FIG. 1B (labeling step). Meanwhile, the steps of the measurement stage include, for example, the step of irradiating the back side of a metal thin film 14 with an incident light and measuring the intensity of fluorescence emitted from the prescribed sandwich type complex formed in the measurement region 38 (measurement step).

In SPFS, a plasmon excitation sensor 16a, which includes a dielectric member 12, a metal thin film 14 formed on the upper surface of the dielectric member 12, and the measurement region 38 formed on the surface of the metal thin film 14, is used. The measurement region 38 is in an area in which reactions for the formation of the prescribed sandwich type complex are performed, and the measurement region 38 is preferably constituted by a SAM 60 formed on the surface of the metal thin film 14, a support 62 bound to the surface of the SAM 60, and the anti-PSA antibody 64 bound to (carried on) the support 62. Such plasmon excitation sensor 16a is prepared in advance prior to the capturing step.

The SAM (Self-Assembled Monolayer) 60 is formed for the purpose of providing a scaffold for linking the support 62 to the surface side of the metal thin film 14 as well as for the purpose of inhibiting metal quenching, which is a phenomenon that the fluorescent material 84, upon coming into contact with the metal thin film 14, stops emitting fluorescence even when irradiated with an excitation light. The SAM 60 is preferably formed of a silane coupling agent which has, at both terminals, a functional group capable of directly or indirectly reacting with the metal thin film 14 and a functional group capable of directly or indirectly reacting with the molecules constituting the support 62.

The support 62 is formed for the purpose of incorporating the anti-PSA antibody 64 into the measurement region 38 at a higher density. That is, when the support 62 is bound to the SAM 60 and the anti-PSA antibody 64 is bound to the support 62, since the support 62 is spatially spread in the height direction, the number of the anti-PSA antibody 64 molecules per unit area (that is, density) can be increased when compared to a case in which the anti-PSA antibody 64 is directly bound to the SAM 60. Such support 62 is preferably made of a hydrophilic polymer inhibiting non-specific adsorption, which has hydrophobic bonding as one cause, and simultaneously having a large number of functional groups capable of reacting with the anti-PSA antibody 64, such as carboxymethyldextran (CMD) in which a large number of carboxyl groups are introduced to the main chain constituted by dextran.

For example, by bringing a solution containing 10-carboxy-1-decanethiol, which is a silane coupling agent, into contact with the surface of the metal thin film 14, the SAM 60 composed of the molecules thereof can be formed. Subsequently, after allowing the SAM 60 thus formed from 10-carboxy-1-decanethiol to react with N-hydroxysuccinimide (NHS) and water-soluble carbodiimide (WSC) and then active esterification of the carboxyl groups oriented on the surface side of the SAM 60, a CMD-containing solution is brought into contact with the SAM 60, and thus the support 62 made of CMD can be immobilized. Furthermore, CMD is allowed to react with NHS and WSC and the carboxyl groups of CMD are subjected to active esterification, after which the resultant is brought into contact with a solution containing the anti-PSA antibody 64, and thus the anti-PSA antibody 64 can be carried in large number on the support 62 made of CMD.

In the capturing step, a specimen containing the LacdiNAc-PSA 100 and a non LacdiNAc-PSA 110 is introduced to a flow channel 36 and thereby brought into contact with the measurement region 38. In the embodiment illustrated in FIG. 1, since the above-described fractionation using a lectin affinity column is not performed in advance, the specimen contains the non LacdiNAc-PSA 110 along with the LacdiNAc-PSA 100. Therefore, not only the LacdiNAc-PSA 100 but also the non LacdiNAc-PSA 110 will be bound to and captured by the anti-PSA antibody 64 in the measurement region 38.

In the labeling step, a solution containing the fluorescence-labeled β-GalNAc affinity molecule 80 is introduced to a flow channel 36 and thereby brought into contact with the measurement region 38. The fluorescence-labeled β-GalNAc affinity molecule 80 binds to the LacdiNAc-PSA 100 captured in the measurement region 38 to form a prescribed sandwich type complex. However, the fluorescence-labeled β-GalNAc affinity molecule 80 does not bind to the non LacdiNAc-PSA 110 having no β-GalNAc residue (except for inevitable binding through non-specific adsorption).

Between the capturing step and the labeling step and after the labeling step, it is preferred to introduce a washing liquid (for example, a surfactant-containing buffer) to the flow channel 36 and thereby remove the non LacdiNAc-PSA 110 or fluorescence-labeled β-GalNAc affinity molecule 80 non-specifically adsorbing to the measurement region 38 (for example, the support 62, the anti-PSA antibody 64, and the SAM 60). In the measurement step, it is preferred to measure the fluorescence intensity in a state in which the flow channel 36 is filled with the washing liquid or a buffer.

SPFS System

Next, one embodiment of an SPFS system suitable for performing the above-described SPFS will be described on the basis of FIG. 2. An SPFS system 1 is constituted by an SPFS measuring member 16, an SPFS measurement apparatus 10, and a control operation apparatus 40.

Figure 2A:
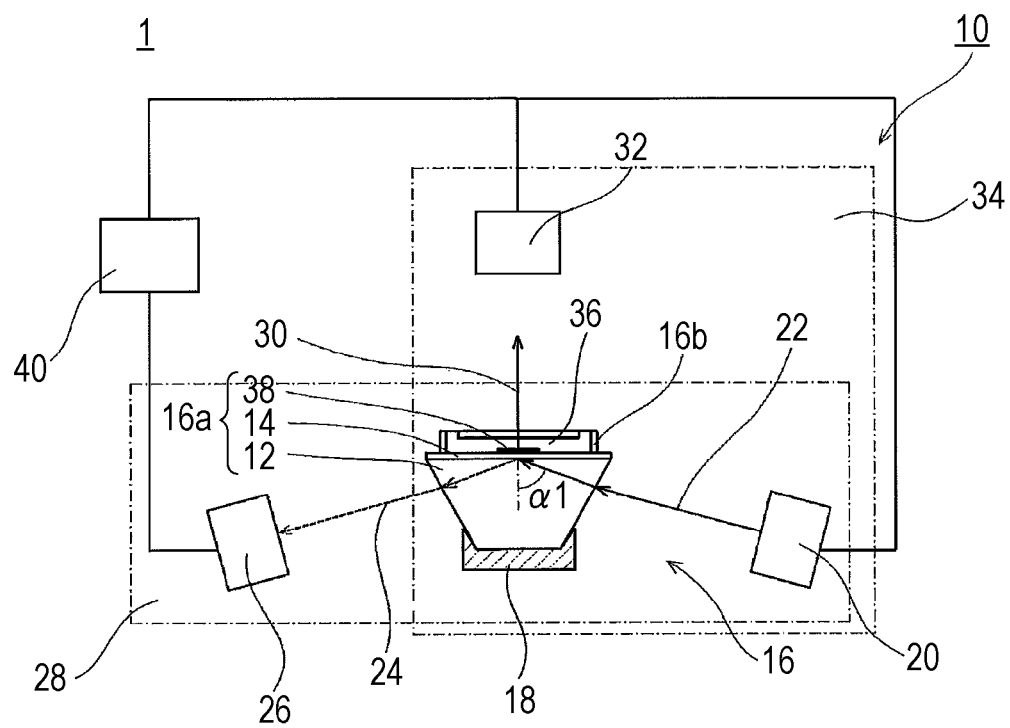
FIG. 2A: An embodiment in which a metal thin film 14 is directly formed on an upper surface of a dielectric member 12 and a plasmon excitation sensor 16a is constituted by the dielectric member 12, the metal thin film 14 and the measurement region 38.
Figure 2B:
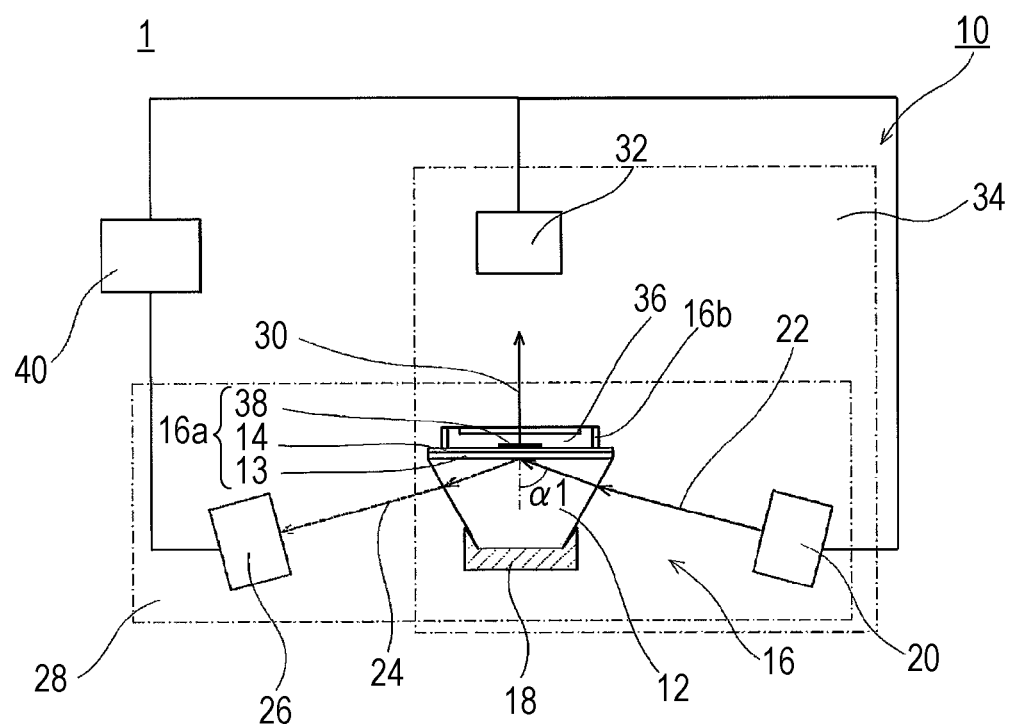
FIG. 2B.

FIG. 2A shows an embodiment in which the metal thin film 14 is directly formed on the upper surface of the dielectric member 12, and a plasmon excitation sensor 16a is constituted by the dielectric member 12, the metal thin film 14 and the measurement region 38. FIG. 2B shows an embodiment in which the metal thin film 14 is formed on the upper surface of a transparent planar substrate 13 that can be separated from the dielectric member 12, and the plasmon excitation sensor 16a is constituted by the transparent planar substrate 13, the metal thin film 14, and the measurement region 38.

The SPFS measuring member 16 is constituted by the plasmon excitation sensor 16a and a flow channel member 16b. A region in which a layer composed of the support 62 and the anti-PSA antibody 64 is formed on a part or the entirety of the upper surface of the plasmon excitation sensor 16a, that is, on a part or the entirety of the bottom surface of the flow channel 36, becomes the measurement region 38. The area of the measurement region 38 is usually adjusted to be equal to or larger than the irradiation area of an incident light 22 which is generally irradiated as laser light and, for example, when the spot diameter of the incident light 22 is about 1 mmφ, the measurement region 38 usually has an area of at least several millimeters square.

The flow channel member 16b is a member for forming the flow channel 36, which has an opening at both ends, above the plasmon excitation sensor 16a, and is made of a colorless and transparent material such as polymethyl methacrylate (PMMA) so that the intensity of a fluorescence 32 can be accurately measured by a fluorescence detection means 32 disposed above the flow channel member 16b. The flow channel member 16b is press-bonded with the plasmon excitation sensor 16a (the dielectric member 12 in FIG. 2A or the transparent planar substrate 13 in FIG. 2B) and, if necessary, an adhesive, a matching oil, a transparent adhesive sheet or the like may be used to inhibit leakage of a solution from a gap therebetween. Further, the flow channel member 16b may be constituted by combining a side wall part (spacer) and a top plate part. In this case, as the side wall part, for example, a sheet-like member which is made of polydimethylsiloxane (PDMS) and has a through-hole serving as a flow channel on the center can be used. As the top plate part, for example, a plate-like member which is made of polymethyl methacrylate (PMMA) and thus colorless and transparent and has two through-holes at the positions corresponding to the respective ends of the through-hole (flow channel) of the side wall part can be used.

In such "flow channel type" SPFS measuring member 16, various solutions such as a specimen, a solution of the fluorescence-labeled β-GalNAc affinity molecule 80, and a washing liquid are introduced to the flow channel 36 through the openings arranged at the respective ends thereof by a liquid transport means (not illustrated) and are allowed to flow in a reciprocating or circulating manner.

Furthermore, when it is not necessary to transport the solutions in a reciprocating or circulating manner, the SPFS measuring member 16 may be of a "well type" in which the solutions are retained. In this case, a well member which can form a well having a larger volume than the flow channel on the upper surface of the plasmon excitation sensor 16a may be used in place of the flow channel member 16b. The upper part of the well may be open, and various liquids can be added to and removed from the well by using, for example, a pipette-like equipment.

The SPFS measurement apparatus 10 basically includes a measuring member mounting section 18, an irradiation means 20, a light-receiving means 26, and a fluorescence detection means 32, and may further include a liquid transport means (not illustrated) as required.

The SPFS measuring member 16 can be either attached to or detached from the measuring member mounting section (stage) 18. When the use of such plasmon excitation sensor 16a including the dielectric member 12 as illustrated in FIG. 2A is postulated, the measuring member mounting section 18 is configured such that the prism-shaped dielectric member 12 can be set thereon. When the use of such plasmon excitation sensor 16a including the transparent planar substrate 13 as illustrated in FIG. 2B is postulated, the prism-shaped dielectric member 12 is set on the measuring member mounting section 18 in advance, and the transparent planar substrate 13 can be tightly mounted on the upper surface of the dielectric member 12.

The liquid transport means (not illustrated) can be constituted by, for example, a pipette-like equipment including a transport means. Various solutions such as specimens and reagents are sucked up from a storing section (not illustrated) thereof, and the thus sucked solution is subsequently discharged through the opening arranged at one end of the flow channel 36 of the flow channel type SPFS measuring member 16, and thus the solution can be introduced to the flow channel 36. As required, a reaction in the measurement region 38 can be facilitated by repeating the suction and discharging operations on this spot to transport a solution in the flow channel 36 in a reciprocating manner. When the SPFS measuring member 16 is of a well type, a solution sucked into the well may be discharged. Further, when the SPFS measuring member 16 is of a flow channel type, the liquid transport means can also be constituted by an external flow channel and a pump. The external flow channel is a member which connects the openings arranged at the respective ends of the flow channel 36 of the SPFS measuring member 16 with the pump. The pump is capable of introducing various solutions, such as specimens and reagents, into the flow channel 36 through this external flow channel and allowing the solutions to flow in a reciprocating or circulating manner.

The irradiation means 20 includes a light source and a light source-moving means and may further include, as required, a polarization filter and a light attenuation filter between the light source and the dielectric member 12. The light source irradiates the incident light 22 which has a wavelength and an intensity that are suitable for exciting the fluorescent material 84 of the fluorescence-labeled lectin, and the light source is generally a laser diode (that is, the incident light 22 is a laser light). The light source-moving means moves the light source in such a manner that the incident light 22 is irradiated, at a prescribed incidence angle α1, to the back side of the metal thin film 14 through a light entering-side surface 12b of the dielectric member 12. The polarization filter is used for having P polarization of the incident light 22 irradiated from the light source so as to allow the metal thin film 14 to efficiently generate surface plasmon resonance. The light attenuation filter is used for adjusting the intensity (photon amount) of the incident light 22 irradiated from the light source such that the fluorescence detection means 32 can acquire a signal value of an appropriate intensity.

The light-receiving means 26 includes a light receiver and a light receiver-moving means. The light receiver receives a reflected light 24, which is the incident light 22 reflected off the back side of the metal thin film 14, and is capable of measuring the intensity of the reflected light 24. The light receiver-moving means is capable of moving the light receiver in synchronization with changes in the incidence angle α1 of the incident light 22 caused by the light source-moving means, such that the light receiver can surely receive the reflected light 24 with varying reflection angles. The most prominent electric field-enhancing effect attributed to surface plasmon resonance is attained when the ratio of the intensity of the reflected light 24 with respect to the intensity of the incident light 22, namely the reflectance, is the lowest, and it is preferred to perform the measurement step of measuring the intensity of the fluorescence at such an incidence angle α1.

The fluorescence detection means 32 includes a detector, a condenser lens, and a filter. The detector is used for receiving the fluorescence 30 emitted from the surface of the plasmon excitation sensor 16a, that is, the fluorescence 30 emitted from the fluorescent material 84 of the fluorescence-labeled lectin captured in the measurement region 38, and measuring the intensity of the fluorescence 30 and, for example, a photomultiplier tube (PMT) can be used. The condenser lens is used for concentrating the fluorescence 30 to the detector and thereby enabling to accurately measure the intensity of the fluorescence 30 and, for example, an objective lens similar to that of a microscope can be used.

The filter is used for allowing only a light that has a wavelength in a prescribed range including the fluorescence 30 to transmit therethrough and reach the detector, and the filter can remove any light that has a wavelength outside the prescribed range and causes a noise, such as scattering light.

Furthermore, the constitution composed of the SPFS measuring member 16 (plasmon excitation sensor 16a), the irradiation means 20, and the light-receiving means 26 may be referred to as "SPR measurement unit 28". The reason for this is because the SPR measurement unit 28 basically shares a common constitution with an apparatus for SPR method (surface plasmon resonance method) which quantifies a substance of interest not by measuring the fluorescence 30 but on the basis of attenuation of the intensity of the reflected light 24 caused by capturing of the substance of interest in the measurement region 38. Meanwhile, the constitution composed of the SPFS measuring member 16 (plasmon excitation sensor 16a), the irradiation means 20, and the fluorescence detection means 32 may be referred to as SPFS measurement unit 34.

The control operation apparatus 40 is connected with the irradiation means 20, the light-receiving means 26, the fluorescence detection means 32 and the liquid transport means (not illustrated) arranged as required, and transmits and receives signals such that the actions of the members of each means can be controlled and information measured by each means can be recorded, stored and calculated. The control operation apparatus 40 can be configured by using a personal computer that is capable of storing programs and information for prescribed control operations.

The control operation apparatus 40 is capable of automatically operating the respective means in accordance with a program such that, for example, the liquid transport means transports solutions such as specimens and reagents in prescribed amounts according to a prescribed order to form a prescribed complex in the measurement region 38; the irradiation means 20 subsequently irradiates the incident light 22 at a prescribed timing and a prescribed incidence angle; and the fluorescence detection means 32 measures the intensity of the fluorescence 30 generated in the measurement region 38. Furthermore, the control operation apparatus 40 may be configured to receive data regarding the intensity of the fluorescence 30 measured for each specimen from the fluorescence detection means 32 followed by storing, and, preferably, to immediately compare the thus-measured values with a prescribed threshold value stored in advance and to further store the estimated Gleason score, or pathological stage, or acquired supplementary information.

[Threshold Values]

The threshold values (cut-off values) that are required for performing the estimation or acquiring information by each method of the present invention based on measured LacdiNAc-PSA content (concentration) in a specimen can be set by a commonly used method which is the same as a known method for estimation or a method for acquiring information, for example, in the same manner as a threshold value for diagnostic marker or tumor marker.

For example, by having as a subject plural patients who have been diagnosed with prostate cancer and undergone gross total removal of prostate, the LacdiNAc-PSA concentration in a blood serum specimen before operation and a Gleason score (primary pattern and secondary pattern) of removed prostate cancer tissues are examined. In general, there is a tendency that the LacdiNAc-PSA concentration is higher as the Gleason score increases (as the malignancy based on primary pattern and secondary pattern increases). By establishing a box plot or an ROC curve (receiver operating characteristic curve) on the basis of measurement results of Gleason score and LacdiNAc-PSA concentration, a threshold value enabling the estimation with desired accuracy can be set. For example, when the method of estimating a Gleason score of the present invention is carried out, the threshold value to estimate whether or not GS is 4+3 or higher is ideally a value allowing that quantification values of LacdiNAc-PSA from a group with GS of 4+3 or higher, which are higher than the threshold value, are as many as possible (that is, high sensitivity), and also quantification values of LacdiNAc-PSA from a group with GS of lower than 4+3 (3+4 or lower), which are higher than the threshold value, are as few as possible (that is, high specificity). On the other hand, the threshold value to estimate whether or not GS is 3+4 or lower is ideally a value allowing that quantification values of LacdiNAc-PSA from a group with GS of 3+4 or lower, which are lower than the threshold value, are as many as possible (that is, high sensitivity), and also quantification values of LacdiNAc-PSA from a group with GS of higher than 3+4 (4+3 or higher), which are lower than the threshold value, are as few as possible (that is, high specificity).

Specifically, when the amount of LacdiNAc-PSA is expressed in U/mL, the cut-off value (threshold value) to estimate that GS is 4+3 or higher is preferably set at 0.05 to 0.31 U/mL. Meanwhile, in order to prevent a possibility of not finding prostate cancer with GS of 4+3 or higher, the cut-off value is preferably set at 0.05 to 0.1 U/mL. The cut-off value for finding first and treat prostate cancer with particularly high risk like GS of 4+3 or higher is preferably set at a value that is higher than 0.1 U/mL but not higher than 0.31 U/mL. The cut-off value to estimate that GS is 3+4 or lower is preferably set at 0.02 to 0.31 U/mL. Meanwhile, when the probability of having prostate cancer with GS of 3+4 or lower is very high and it is intended to obtain supplementary information for observing development over time and diagnosis, the cut-off value is preferably set at 0.02 to 0.1 U/mL.

In conjunction with a change in threshold value, the sensitivity and specificity also vary, and thus adjustment (optimization) is preferably carried out to have balance between them. A threshold value with high reliability can be set by increasing the number of samples as a population group of measurement data. By comparing the threshold value which is set as described with a measurement value of content of LacdiNAc-PSA (concentration) in a certain specimen, supplementary information for estimating a Gleason score can be obtained. For example, when a measurement value of content of LacdiNAc-PSA (concentration) is not lower than the threshold value, the prostate cancer patient from which the specimen has been collected has a Gleason score of 4+3 or higher, or, when a measurement value is lower than the threshold value, a Gleason score is 3+4 or lower, and thus supplementary information for having an estimation with prescribed probability (sensitivity and specificity) can be obtained.

In the same manner as those described above, it is possible to set a threshold value for estimating that pT is 3 or higher or pT is 2 or lower with regard to the method for estimating a pathological stage (pT) of the present invention.

Specifically, when the amount of LacdiNAc-PSA is expressed in U/mL, the cut-off value to estimate that pT is 3 or higher is preferably set at 0.06 to 1.24 U/mL. Furthermore, in order to prevent a possibility of not finding prostate cancer with pT of 3 or higher, the cut-off value is preferably set at 0.06 to 0.1 U/mL. The cut-off value for finding first and treat prostate cancer with particularly high risk like pT of 3 or higher is preferably set at 0.25 to 1.24 U/mL.

The cut-off value to estimate that pT is 2 or lower is preferably set at 0.03 to 0.23 U/mL. Furthermore, when the probability of having prostate cancer with pT of 2 or lower is very high and it is intended to obtain supplementary information to determine the necessity of having surgical application or the like, the cut-off value is preferably 0.03 to 0.12 U/mL. In general, there is a tendency that a higher quantification value of LacdiNAc-PSA is obtained as pT increases.

Furthermore, the threshold values with regard to the method for acquiring supplementary information of the present invention can be also set in the same manner as those described above. In general, when an index relating to pathological diagnosis like GS based on biopsy is underestimated (index using removed prostate tissues is higher than index obtained by biopsy), there is a tendency that a higher quantification value of LacdiNAc-PSA is yielded.

With regard to the method of quantifying a glycoprotein having a sugar chain containing a specific sugar residue, such as LacdiNAc-PSA, particularly the quantification method based on an SPFS method, and the method of obtaining specific information that can be used in diagnosis and the like in which the thus-obtained content is compared with a prescribed threshold value, reference can be made to, for example, WO 2010/090264 (Patent Literature 3) and JP 2013-076666A (Patent Literature 4) for general matters and variations of embodiments other than those described in the present specification.

—Kit—

In order to carry out efficiently each method of the present invention, a kit may be constituted by combining necessary reagents. The kit includes at least reagents and labwares for measuring the concentration of LacdiNAc-PSA in a specimen like blood serum, in which the measurement is carried out for each method of the present invention. For measurement of the concentration of LacdiNAc-PSA, a quantification method based on sandwich type assay like SPFS or ELISA is typically used, and, if necessary, a fractionation method using a lectin affinity column is used in combination. Thus, the kit typically has, as main constituents, reagents for forming an immunocomplex of sandwich type suitable for those methods, namely, anti-PSA antibody for immobilization and β-GalNAc residue-affinity molecule (prescribed lectin like WFA, or anti β-GalNAc antibody) for detecting LacdiNAc-PSA, and, if necessary, lectin or the like for preparing a lectin affinity column can be also included as a constituent.

The kit for carrying out each method of the present invention may include a reagent other than the reagents described above, a labware, a user's guidebook or the like. Examples of the reagent and labware include a reagent for immobilizing a prescribed antibody on a surface of a sensor chip for SPFS or a substrate for ELISA, a reagent for biding a fluorescent material to prescribed lectin or antibody, a blocking solution for suppressing non-specific adsorption on a surface of a sensor chip for SPFS or a substrate for ELISA, a washing solution for transporting liquid after transporting a blood specimen or a reagent in each step of SPFS, a reagent for binding prescribed lectin to a carrier of a lectin affinity column, a reagent for preparing a buffer solution for washing or elution for a lectin affinity column, a treatment solution for a blood specimen, a labware for reacting those reagents, a sensor chip for SPFS or a substrate for ELISA, and a carrier of a lectin affinity column. Furthermore, in a user's guidebook, information required for performing each method of the present invention, for example, a method of using the above reagents and labware (protocol), a threshold value corresponding to each method, or the like can be described.

EXAMPLES (1) Assembly of SPFS Measurement Apparatus

An SPFS measurement apparatus according to the embodiment illustrated in FIG. 2B was uniquely assembled and used in the below-described Examples. As the light source of the irradiation means 20, a laser diode (LD) capable of irradiating a light having a wavelength of 635 nm was used, and a light attenuation filter (neutral density filter) was arranged between the light source and the dielectric member 12 so that the photon amount could be adjusted. As the dielectric member 12, a prism of 60 degrees (manufactured by SIGMAKOKI CO., LTD.) was used. On the upper surface of this dielectric member 12, the measuring member 16 was constructed by fixing a member (sensor chip) constituted by the plasmon excitation sensor 16a including the transparent planar substrate 13 and the flow channel member 16b, which member was produced in the below-described manner. A photomultiplier tube (PMT) was used as a photodetector of the fluorescence detection means 32, and an objective lens was arranged as the condenser lens.

(2) Production of Flow Channel Type SPFS Measuring Member

After plasma-cleaning of a planar substrate made of glass having a refractive index of 1.72 and a thickness of 1 mm ("S-LAL 10", manufactured by Ohara Inc.), a chromium thin film was formed on one side of this substrate by sputtering. After that, a gold thin film was further formed on the surface of this chromium thin film by sputtering. The chromium thin film had a thickness of 1 to 3 nm, and the gold thin film had a thickness of 44 to 52 nm.

The substrate having the gold thin film formed in this manner was immersed in an ethanol solution containing 1 mM of 10-carboxy-1-decanethiol for at least 24 hours to form a SAM composed of the molecules on the surface of the gold thin film. The substrate was then removed from the solution and washed with ethanol and isopropanol, after which the substrate was dried using an air gun.

On this substrate, a 25 mM MES-buffered physiological saline, which contained 0.5 mM of N-hydroxysuccinimide (NHS), 0.5 mM of water-soluble carbodiimide (WSC) and 1 mg/mL of carboxymethyldextran (CMD) ("CMD-500-06I4", manufactured by Meito Sangyo Co., Ltd.: average molecular weight=500,000, degree of substitution=0.51), and a 10 mM NaCl solution (pH 6.0) were applied dropwise in an amount of 0.8 mL each and allowed to react for 20 minutes so as to bind CMD to SAM, and thus a CMD film was formed on the surface of the plasmon excitation sensor.

On this plasmon excitation sensor having the formed CMD film, a 0.5 mm-thick spacer made of polydimethylsiloxane (PDMS) having a through hole of 2 mm in width and 14 mm in length was mounted. A 2 mm-thick top plate made of polymethyl methacrylate (PMMA), which had through-holes at the positions corresponding to the respective ends of the through-hole of the spacer, was further disposed thereon. The plasmon excitation sensor, the spacer and the top plate were press-bonded and screw-fixed, and thus a flow channel type SPFS measuring member including a flow channel constituted by the through-hole of the spacer through which specimens, reagents and the like could be transported via the through-hole of the top plate was prepared.

(3) Preparation of Antibody (Anti-PSA Monoclonal Antibody) Immobilized Substrate An external flow channel and a peristaltic pump were connected to the flow channel type SPFS measuring member which has been produced as described above, and ultrapure water and then phosphate buffered saline (PBS) were circulated for 10 minutes and 20 minutes, respectively, at room temperature (25° C.) and a flow rate of 500 μL/min, and thus the surface of the plasmon excitation sensor was equilibrated.

Subsequently, after circulating 5 mL of a phosphate buffered saline (PBS) containing 50 mM of N-hydroxysuccinimide (NHS) and 100 mM of water-soluble carbodiimide (WSC) for 20 minutes, 2.5 mL of an anti-PSA monoclonal antibody solution was circulated for 30 minutes so as to allow the antibody to bind to CMD, and thus an anti-PSA monoclonal antibody-immobilized CMD film (measurement region) was prepared. Thereafter, by circulating a phosphate buffered saline (PBS) containing 1% by weight of bovine serum albumin (BSA) for 30 minutes, a treatment for preventing non-specific adsorption in the flow channel was carried out.

(4) Preparation of Fluorescence-Labeled Lectin (Alexa Fluor 647-Labeled WFA)

The indicated fluorescence-labeled lectin was produced using a fluorescent material labeling kit, "Alexa Fluor (registered trademark) 647 Protein Labeling Kit" (manufactured by Invitrogen Corp.). After mixing 100 μg-equivalent of WFA ("L-1350", manufactured by Vector Laboratories, Inc.) with 0.1 M sodium bicarbonate and an Alexa Fluor 647 reactive dye that are contained in the kit, and allowing them to react at room temperature for 1 hour, the resultant was subjected to gel filtration chromatography and ultrafiltration, and thus the Alexa Fluor 647 reactive dye that was not utilized for labeling was removed and a fluorescence-labeled WFA lectin was obtained. Thereafter, the absorbance was measured to quantify the concentration of the indicated fluorescence-labeled lectin.

(5) Quantification of LacdiNAc-PSA in Blood Serum Specimen

By having as a subject 92 patients who have been diagnosed with prostate cancer and had gross total removal of prostate, concentration of LacdiNAc-PSA and concentration of total PSA in a blood serum specimen before operation were quantified. Backgrounds of the patients are described in Table 1. Quantification of the LacdiNAc-PSA concentration was carried out by SPFS by using a flow channel type SPFS measuring member which is provided with a substrate immobilized with an anti-PSA monoclonal antibody, and a fluorescent-labeled WFA, that are prepared as described above. Details of the order are as follows. Meanwhile, concentration of the total PSA was quantified by a prescribed method by using "ARCHITECT Analyzer i1000SR" system and a prostate specific antigen kit, "Total PSAΨAbbott" (manufactured by Abbott Japan Co., Ltd.).

TABLE 1

| | PCa who underwent RP | P |
|---|---|---|
| n | 92 | a vs b |
| Age, median (range) | 68 (44-85) | |
| Total PSA, ng/mL, median (range) | 9.56 (3.26-62.62) | |
| GS ≤ 3 + 4[a] | 7.69 (4.02-15.49) | <0.001 |
| GS ≥ 4 + 3[b] | 9.61 (3.26-62.62) | |
| PSA-Gi U/mL, median (range) | 0.165 (0.0230-1.593) | |

TABLE 1-continued

| | PCa who underwent RP | P |
|---|---|---|
| GS ≤ 3 + 4[a] | 0.0985 (0.0490-0.293) | <0.001 |
| GS ≥ 4 + 3[b] | 0.1885 (0.0230-1.593) | |
| Pathological T stage, n (%) | | |
| pT1 | 4 (4.3) | |
| pT2 | 53 (57.6) | |
| pT3 | 38 (41.3) | |
| Biopsy GS, n (%) | | |
| 3 + 3 | 3 (3.3) | |
| 3 + 4 | 27 (29.3) | |
| 4 + 3 | 11 (12.0) | |
| 3 + 5 | 2 (2.2) | |
| 4 + 4 | 13 (14.1) | |
| 5 + 3 | 0 (0) | |
| 4 + 5 | 28 (45.2) | |
| 5 + 4 | 8 (8.7) | |
| 5 + 5 | 0 (0) | |
| Ope GS, n (%) | | |
| 3 + 3 | 1 (1.1) | |
| 3 + 4 | 13 (14.1) | |
| 4 + 3 | 14 (15.2) | |
| 3 + 5 | 3 (3.2) | |
| 4 + 4 | 9 (9.8) | |
| 5 + 3 | 1 (1.1) | |
| 4 + 5 | 37 (40.2) | |
| 5 + 4 | 12 (13.0) | |
| 5 + 5 | 2 (2.2) | |

PCa: Prostate Cancer patients,
RP: prostatectomy
Biopsy GS: Gleason Score in Biopsy,
Ope GS: Gleason Score after RP.

100 μL of a dilution solution was added to 20 μL of a test specimen (blood serum specimen), and the resultant was thoroughly stirred in a test tube to prepare a mixed solution. This mixed solution in an amount of 100 μL was circulated in the flow channel and allowed to react with the measurement region for 60 minutes. After that, TBS (TBS-T) containing 0.05% by weight of "Tween (registered trademark) 20" was transported and washing was carried out for 3 minutes. Next, 100 μL of the Alexa Fluor 647-labeled WFA solution (WFA concentration: 10 μg/mL) was circulated in the flow channel to allow the solution to react with the measurement region for 10 minutes. Then, TBS-T was transported again and washing was carried out for 5 minutes. Thereafter, with the flow channel being filled with this TBS-T, an excitation light was irradiated thereto and the fluorescence intensity (signal) of Alexa Fluor 647 was measured by SPFS.

Based on a calibration curve prepared from prepared specimens having known concentrations of LacdiNAc-PSA, the measured fluorescence intensity value of each test specimen was converted to the concentration of LacdiNAc-PSA. Furthermore, according to a general method, staging a Gleason score (GS) at biopsy of the patient for each test specimen, and staging of a Gleason score (GS) and pathological stating (pT) after gross total removal from the patient for each test specimen were also carried out.

(i) Between a patient group in which GS is 3+4 or lower and a patient group in which GS is 4+3 or higher with regard to the removed prostate tissues, concentration distribution of LacdiNAc-PSA and total PSA in a blood serum specimen was compared. The results are shown in FIGS. 3A and 3B. It was shown that, compared to a patient group in which GS is 3+4 or lower, concentration of LacdiNAc-PSA in a blood serum specimen is higher in significant sense in a patient group in which GS is 4+3 or higher (Mann-Whitney U test, P<0.05). Meanwhile, with regard to the total PSA concentration in a blood serum specimen, a significant difference was not recognized between the two groups.

The ROC curve established based on the above results is shown in FIG. 3C, and the cut-off values and hit ratio (prediction performance) obtained therefrom regarding the concentration of LacdiNAc-PSA in blood serum specimen in relation to those with GS of 4+3 or higher and those with GS of 3+4 or lower are summarized in Table 2 and Table 3, respectively. Based on those results, it is understood that a person who is skilled in the art can set an appropriate threshold value and carry out the method for estimating a GS of the present invention.

TABLE 2

| Cut-off value of LacdiNAc-PSA (U/mL) | Sensitivity (%) for Gleason score of 4 + 3 or higher | Specificity (%) for Gleason score of 4 + 3 or higher |
| --- | --- | --- |
| 0.3095 or higher | 30.77 | 100.00 |
| 0.2425 or higher | 41.03 | 92.86 |
| 0.1335 or higher | 64.10 | 78.57 |
| 0.1130 or higher | 70.51 | 64.29 |
| 0.0970 or higher | 76.92 | 50.00 |
| 0.0715 or higher | 84.62 | 35.71 |
| 0.0600 or higher | 91.03 | 21.43 |
| 0.0510 or higher | 94.87 | 14.29 |

TABLE 3

| Cut-off value of LacdiNAc-PSA (U/mL) | Sensitivity (%) for Gleason score of 3 + 4 or lower | Specificity (%) for Gleason score of 3 + 4 or lower |
| --- | --- | --- |
| Less than 0.0290 | 0.00 | 98.72 |
| Less than 0.0510 | 14.29 | 94.87 |
| Less than 0.0600 | 21.43 | 91.03 |
| Less than 0.0715 | 35.71 | 84.62 |
| Less than 0.0970 | 50.00 | 76.92 |
| Less than 0.1130 | 64.29 | 70.51 |
| Less than 0.1335 | 78.57 | 64.10 |
| Less than 0.2425 | 92.86 | 41.03 |
| Less than 0.3095 | 100.00 | 30.77 |

(II) Based on a GS transition over time from GS at biopsy to GS after gross total removal, the patients were classified, and concentration of LacdiNAc-PSA in blood serum specimen from each patient group was compared. The results are shown in FIG. 4. A case in which GS is lower (down-graded) after gross total removal compared to GS at biopsy is marked with ■, a case in which GS is higher (up-graded) after gross total removal compared to GS at biopsy is marked with ●, and a case in which no difference is shown between them is marked with ▲. The up-graded case tends to have higher concentration of LacdiNAc-PSA while the down-graded case tends to have lower concentration of LacdiNAc-PSA. Based on those results, it is understood that a person who is skilled in the art can set an appropriate threshold value and carry out the method for acquiring supplementary information of the present invention.

(iii) Between a patient group in which pT is 2 or lower and a patient group in which pT is 3 or higher, concentration distribution of LacdiNAc-PSA in a blood serum specimen was compared. The results are shown in FIGS. 5A and 5B. It was shown that, compared to a patient group in which pT is 2 or lower, concentration of LacdiNAc-PSA and concentration of total PSA in a blood serum specimen are higher in significant sense in a patient group in which pT is 3 or higher (Mann-Whitney U test, P<0.05).

The ROC curve established based on the above results is shown in FIG. 5C, and the cut-off values and hit ratio (prediction performance) obtained therefrom regarding the concentration of LacdiNAc-PSA in blood serum specimen in relation to those with pT of 3 or higher and those with pT of 2 or lower are summarized in Table 4 and Table 5, respectively. Based on those results, it is understood that a person who is skilled in the art can set an appropriate threshold value and carry out the method for estimating a pT of the present invention.

TABLE 4

| Cut-off value of LacdiNAc-PSA (U/mL) | Sensitivity (%) for pT of 3 or higher | Specificity (%) for pT of 3 or higher |
| --- | --- | --- |
| 1.233 or higher | 2.632 | 94.44 |
| 0.6540 or higher | 10.53 | 92.59 |
| 0.5755 or higher | 15.79 | 90.74 |
| 0.4235 or higher | 18.42 | 88.89 |
| 0.3925 or higher | 21.05 | 87.04 |
| 0.3590 or higher | 23.68 | 81.48 |
| 0.3290 or higher | 31.58 | 79.63 |
| 0.2555 or higher | 39.47 | 70.37 |
| 0.2245 or higher | 44.74 | 66.67 |
| 0.1850 or higher | 63.16 | 66.67 |
| 0.1380 or higher | 65.79 | 50.00 |
| 0.1105 or higher | 76.32 | 40.74 |
| 0.0870 or higher | 84.21 | 31.48 |
| 0.0715 or higher | 92.11 | 25.93 |
| 0.0655 or higher | 94.74 | 18.52 |

TABLE 5

| Cut-off value of LacdiNAc-PSA (U/mL) | Sensitivity (%) for pT of 2 or lower | Specificity (%) for pT of 2 or lower |
| --- | --- | --- |
| Less than 0.0375 | 3.704 | 100.00 |
| Less than 0.0455 | 5.556 | 97.37 |
| Less than 0.0475 | 7.407 | 97.37 |
| Less than 0.0540 | 11.11 | 94.74 |
| Less than 0.0675 | 18.52 | 92.11 |
| Less than 0.0740 | 25.93 | 89.47 |
| Less than 0.0815 | 29.63 | 86.84 |
| Less than 0.0840 | 29.63 | 84.21 |
| Less than 0.0905 | 31.48 | 81.58 |
| Less than 0.1200 | 42.59 | 71.05 |
| Less than 0.1885 | 66.67 | 60.53 |
| Less than 0.2245 | 66.67 | 44.74 |

Reference Example

With regard to the concentration of LacdiNAc-PSA in a blood serum specimen before biopsy from 191 patients who have been diagnosed with prostate cancer in which the concentration is measured as described above, relationship with a GS of tissues collected by biopsy and combination of primary pattern and secondary pattern of each was examined. The results are shown in FIG. 6. It is shown that, as the LacdiNAc-PSA concentration in a blood serum specimen before biopsy increases, the malignancy based on combination of primary pattern and secondary pattern also tend to increase.

REFERENCE SIGNS LIST

1 SPFS system
10 SPFS measuring apparatus
12 Dielectric member
13 Transparent planar substrate
14 Metal thin film 16 SPFS measuring member (flow channel type)
16a Plasmon excitation sensor
16b Flow channel member
18 Measuring member mounting section
20 Irradiation means
22 Incident light
24 Reflected light
26 Light-receiving means
28 SPR measurement unit
30 Fluorescence
32 Fluorescence detection means
34 SPFS measurement unit
36 Flow channel
38 Measurement region
40 Control operation means
60 SAM
62 Support
64 Anti-PSA antibody
80 Fluorescence-labeled β-GalNAc-affinity molecule
82 β-GalNAc-affinity molecule
84 Fluorescent material
100 LacdiNAc-PSA
102 PSA protein
104 Sugar chain having GalNAc residue at non-reducing terminal
104a β-GalNAc
110 Non LacdiNAc-PSA
114 Sugar chain not having GalNAc at non-reducing terminal

The invention claimed is:

1. A method for determining a Gleason score (GS) that represents the malignancy of prostate cancer, said method comprising:

measuring content of prostate specific antigen (PSA) having a β-N-acetylgalactosamine residue at a non-reducing terminal of a sugar chain in a specimen, wherein quantification of the PSA is carried out by using a surface plasmon-field enhanced fluorescence spectroscopy (SPFS), comparing the measured content of PSA having a β-N-acetylgalactosamine residue to a first threshold value for a GS of 3+4 or lower, or comparing the measured content of PSA having a β-N-acetylgalactosamine residue to a second threshold value for a GS of 4+3 or higher, and determining that the specimen has a GS of 4+3 or higher when the measured value of PSA having a β-N-acetylgalactosamine residue is not less than the second threshold value, or determining that the specimen has a GS of 3+4 or lower when the measured value of PSA having a β-N-acetylgalactosamine residue is less than the first threshold value, wherein GS is estimated to be 4+3 or higher when the measured value of PSA having a β-N-acetylgalactosamine residue is set at 0.05 to 0.31 U/ml, and GS is estimated to be 3+4 or lower when the measured value of PSA having a β-N-acetylgalactosamine residue is set at 0.02 to 0.31 U/ml, wherein quantification of the PSA is carried out by a method including binding a molecule having an affinity for a β-N-acetylgalactosamine residue to the PSA, and wherein the molecule having an affinity for a β-N-acetylgalactosamine residue is *Wisteria floribunda* lectin (WFA), soybean agglutinin (SBA), *Vicia Villosa* lectin (VVL), or an anti-β-N-acetylgalactosamine antibody.

2. A method for determining a pathological stage (pT) that represents the progress of prostate cancer, said method comprising:

measuring content of prostate specific antigen (PSA) having a β-N-acetylgalactosamine residue at a non-reducing terminal of a sugar chain in a specimen, wherein quantification of the PSA is carried out by using a surface plasmon-field enhanced fluorescence spectroscopy (SPFS), comparing the measured content of PSA having a β-N-acetylgalactosamine residue to a first threshold value for a pT of 2 or lower, or comparing the measured content of PSA having a β-N-acetylgalactosamine residue to a second threshold value for a pT of 3 or higher, and determining that the specimen has a pT of 3 or higher when the measured value of PSA having a β-N-acetylgalactosamine residue is not less than the second threshold value, or determining that the specimen has a pT of 2 or lower when the measured value of PSA having a β-N-acetylgalactosamine residue is less than the first threshold value, wherein pT is estimated to be 3 or higher when the measured value of PSA having a β-N-acetylgalactosamine residue is set at 0.06 to 1.24 U/ml, and pT is estimated to be 2 or lower when the measured value of PSA having a β-N-acetylgalactosamine residue is set at 0.03 to 0.23 U/ml, wherein quantification of the PSA is carried out by a method including binding a molecule having an affinity for a β-N-acetylgalactosamine residue to the PSA, and wherein the molecule having an affinity for a β-N-acetylgalactosamine residue is *Wisteria floribunda* lectin (WFA), soybean agglutinin (SBA), *Vicia Villosa* lectin (VVL), or an anti-β-N-acetylgalactosamine antibody.

* * * * *